United States Patent [19]

Talley et al.

[11] Patent Number: 5,908,852

[45] Date of Patent: Jun. 1, 1999

[54] 1,3,5 TRISUBSTITUTED PYRAZOLE COMPOUNDS FOR TREATMENT OF INFLAMMATION

[75] Inventors: John J Talley; Donald J Rogier, Jr., both of St. Louis, Mo.; Thomas D. Penning, Elmhurst; Stella S Yu, Morton Grove, both of Ill.

[73] Assignee: G. D. Searle & Co., Skokie, Ill.

[21] Appl. No.: 08/647,911

[22] PCT Filed: Nov. 14, 1994

[86] PCT No.: PCT/US94/12722

§ 371 Date: May 30, 1996

§ 102(e) Date: May 30, 1996

[87] PCT Pub. No.: WO95/15318

PCT Pub. Date: Jun. 8, 1995

Related U.S. Application Data

[63] Continuation of application No. 08/160,517, filed as application No. PCT/US94/12722, Nov. 14, 1994, Pat. No. 5,434,178.

[51] Int. Cl.[6] .................. A61K 31/415; C07D 231/12; C07D 405/04; C07D 405/09
[52] U.S. Cl. ................ 514/340; 514/222.2; 514/227.2; 514/227.8; 514/252; 514/256; 514/274; 514/278; 514/359; 514/381; 514/383; 514/397; 514/406; 514/407; 544/3; 544/55; 544/58.5; 544/60; 544/333; 544/405; 546/272.1
[58] Field of Search .................. 544/3, 55, 60, 544/333, 405, 58.5; 546/272.1; 548/235, 247, 254, 255, 266.2, 312.4, 364.1, 365.4, 365.7; 514/406, 407, 340

[56] References Cited

U.S. PATENT DOCUMENTS

| | | | |
|---|---|---|---|
| 3,254,093 | 5/1966 | Huisgen et al. | 260/295 |
| 4,146,721 | 3/1979 | Rainer | 548/374 |
| 5,134,142 | 7/1992 | Matsuo et al. | 514/255 |
| 5,401,765 | 3/1995 | Lee | 548/406 |
| 5,434,178 | 7/1995 | Talley et al. | 514/406 |
| 5,466,823 | 11/1995 | Talley et al. | 548/377.1 |
| 5,475,018 | 12/1995 | Lee et al. | 514/406 |

OTHER PUBLICATIONS

H. Faidallah et al, Pak. J. Sci. Ind. Res., 35, 213 (1992).

H. Mokhtar et al, Pak. J. Sci. Ind. Res., 35, 428 (1992).

H. Faid–Allah et al, Ind. J. Chem., 27B, 245 (1988).

R. Soliman et al, J. Pharm. Sci., 76, 626 (1987).

H. Faidallal et al, Pak. J. Sci. Ind. Res., 35, 8 (1992).

R. Soliman et al, J. Pharm. Sci., 70, 606 (1981).

Chemical Abstracts, 121:11 (1994).

*Primary Examiner*—Richard L. Raymond
*Attorney, Agent, or Firm*—Joseph W. Bulock

[57] ABSTRACT

A class of 1,3,5-substituted pyrazoles is described for the treatment of inflammation, including treatment of pain and disorders such as arthritis. Compounds of particular interest are of Formula I

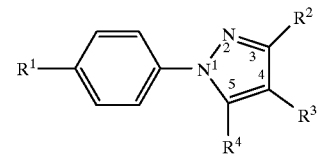

wherein $R^1$, $R^2$, $R^3$ and $R^4$ are as described herein; or a pharmaceutically-acceptable salt thereof.

17 Claims, No Drawings

1,3,5 TRISUBSTITUTED PYRAZOLE COMPOUNDS FOR TREATMENT OF INFLAMMATION

RELATED CASES

This is an application under 35 USC §371 of International Application PCT/US94/12722, with an international filing date of November 14, 1994, which is a continuation-in-part of U.S. patent application Ser. No. 08/160,517, filed Nov. 30, 1993, now issued as U.S. Pat. No. 5,434,178.

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase II (COX II)" or "prostaglandin G/H synthase II") provides a viable target of inhibition which more effectively reduces inflammation and produces fewer and less drastic side effects.

Pyrazole compounds have been used in the treatment of inflammation. U.S. Pat. No. 5,134,142 to Matsuo et al describes 1,5-diaryl pyrazoles, and more particularly, 1-(4-fluorophenyl)-5-[4-(methylsulfonyl)phenyl]-3-(5-tetrazolyl)pyrazole, as having anti-inflammatory activity.

U.S. Pat. No. 4,146,721 to Rainer describes 1,3,5-triphenyl pyrazoles as useful analgesics, anti-inflammatory agents and antipyretics, and specifically describes 1,3,5-triphenyl-pyrazol-4-acetamide.

U.S. Pat. No. 3,254,093 to Huisgen et al describes a process for preparing pyrazoles, including ethyl-[1,3,5-triphenyl-1H-pyrazole-4-carboxylate.

The synthesis of a series of [3-phenyl-5-(2-phenyltriazol-4-yl)]-1H-pyrazol-1-yl]benzenesulfonamides is described [H. Faidallah et al, *Pak. J. Sci. Ind. Res.*, 35, 213 (1992)], and specifically 4-[4-bromo-3-(4-methylphenyl)-5-(2-phenyl-2H-1,2,3-triazol-4-yl)-1H-pyrazol-1-yl]benzenesulfonamide. The synthesis of a series of related triazole substituted pyrazolyl benzenesulfonamides has been described [H. Mokhtar et al, *Pak. J. Sci. Ind. Res.*, 35, 428 (1992)].

The use of 4-[3-(4-aminophenyl)-5-phenyl-1H-pyrazol-1-yl]benzenesulfonamide as an intermediate in the synthesis of the corresponding benzenesulfonylureas has been described [H. Faid-Allah et al, *Ind. J. Chem.*, 27B, 245 (1988)]. An intermediate for antidiabetic agents, 4-[3-phenyl-5-bromophenyl-1H-pyrazol-1-yl]benzenesulfonamide, has been described [R. Soliman et al, *J. Pharm. Sci.*, 76, 626 (1987)]. The condensation of sulfamylphenylhydrazines with chalcones to produce 4-[3,5-diphenyl-pyrazol-1-yl]benzenesulfonamides has been reported, which are potential hypoglycemic agents [H. Faidallah et al, *Pak. J. Sci. Ind. Res.*, 35, 8 (1992)]. Specifically, 4-[3,5-bis(4-methoxyphenyl)-1H-pyrazol-1-yl]benzenesulfonamide is described. 4-[3,5-Diphenyl-1H-pyrazol-1-yl]benzenesulfonamide has been produced and evaluated for antidiabetic activity [R. Soliman et al, *J. Pharm. Sci.*, 70, 606 (1981)].

DESCRIPTION OF THE INVENTION

A class of compounds useful in the treatment of inflammation-related disorders is defined by Formula I:

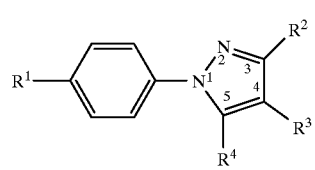

wherein $R^1$ is alkylsulfonyl or sulfamyl; wherein $R^2$ is aryl or heterocyclic; wherein $R^2$ is optionally substituted at a substitutable position with one or more radicals selected from halo, alkoxy, alkyl, nitro, alkylthio, amino, haloalkyl, hydroxyl, carboxyl, N-monoalkylamino, N,N-dialkylamino, cyano, alkoxycarbonyl and acylamino; wherein $R^3$ is selected from hydrido, alkyl, haloalkyl, cyano, carboxyl, alkoxycarbonyl, amino, acyl, acylamino, halo and alkylsulfonylamino; wherein $R^4$ is aryl or heterocyclic; wherein $R^4$ is optionally substituted at a substitutable position with one or more radicals selected from halo, alkoxy, alkyl, nitro, alkylthio, amino, haloalkyl, hydroxyl, carboxyl, N-monoalkylamino, N,N-dialkylamino, cyano, alkoxycarbonyl and acylamino; provided at least one of $R^2$ and $R^4$ cannot be phenyl or substituted triazole, when $R^1$ is sulfamyl; further provided $R^2$ cannot be 4-methoxyphenyl or 4-methylphenyl when $R^4$ is 4-methoxyphenyl or 4-methylphenyl, and when $R^1$ is sulfamyl; and further provided that $R^2$ cannot be tetrazole when $R^4$ is fluorophenyl, and when $R^1$ is methylsulfonyl; or a pharmaceutically-acceptable salt thereof.

The phrase "further provided", as used in the above description, is intended to mean that the denoted proviso is not to be considered conjunctive with any of the other provisos.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthropathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects.

The present invention preferably includes compounds which selectively inhibit cyclooxygenase II over cyclooxygenase I and do not significantly inhibit one or more other arachidonic pathway steps.

Preferably, the compounds have a cyclooxygenase II $IC_{50}$ of less than about 0.1 $\mu$M, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 0.5 $\mu$M, and more preferably of greater than 5 $\mu$M. Such preferred selectivity may indicate an ability to reduce the incidence of common NSAID-induced side effects.

A preferred class of compounds embraced by Formula I consists of those compounds wherein $R^1$ is lower alkylsulfonyl or sulfamyl; wherein $R^2$ is aryl or heteroaryl; wherein $R^2$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein $R^3$ is selected from hydrido, lower alkyl, lower haloalkyl, cyano, carboxyl, alkoxycarbonyl, amino, acyl, acylamino, halo and alkylsulfonylamino; wherein $R^4$ is aryl or heteroaryl; wherein $R^4$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; or a pharmaceutically-acceptable salt thereof.

A more preferred class of compounds embraced by Formula I consists of those compounds wherein $R^1$ is lower alkylsulfonyl; wherein $R^2$ is aryl or heteroaryl; wherein $R^2$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein $R^3$ is selected from hydrido, lower alkyl, lower haloalkyl, cyano, carboxyl, alkoxycarbonyl, amino, acyl, acylamino, halo and alkylsulfonylamino; wherein $R^4$ is aryl or heteroaryl; wherein $R^4$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; provided that $R^2$ cannot be tetrazole when $R^4$ is fluorophenyl; or a pharmaceutically-acceptable salt thereof.

A class of compounds of particular interest consists of those compounds of Formula I wherein $R^1$ is methylsulfonyl; wherein $R^2$ is selected from phenyl, pyrryl, furyl, pyridyl, pyrimidyl, pyrazinyl, pyrazolyl, oxazolyl, isoxazolyl, imidazolyl, thiazyl, pyranyl and thienyl; wherein $R^2$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl and acetamido; wherein $R^3$ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH$—; wherein $R^4$ is selected from phenyl, pyrryl, furyl, pyridyl, pyrimidyl, pyrazinyl, pyrazolyl, oxazolyl, isoxazolyl, imidazolyl, thiazyl, pyranyl and thienyl; wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl and acetamido; or a pharmaceutically-acceptable salt thereof.

A family of specific compounds of particular interest within Formula I consists of compounds, and pharmaceutically-acceptable salts thereof, as follows:

3,5-bis(4-chlorophenyl)-1-(4-methylsulfonylphenyl)-1H-pyrazole;

5-(4-chlorophenyl)-3-(3,5-difluorophenyl)-1-(4-methylsulfonylphenyl)-1H-pyrazole;

5-(4-chlorophenyl)-3-(2,5-difluorophenyl)-1-(4-methylsulfonylphenyl)-1H-pyrazole;

5-(4-chlorophenyl)-3-(3,4-difluorophenyl)-1-(4-methylsulfonylphenyl)-1H-pyrazole;

5-(4-chlorophenyl)-3-(4-methoxyphenyl)-1-(4-methylsulfonylphenyl)-1H-pyrazole;

3-(3-chlorophenyl)-5-(4-chlorophenyl)-1-(4-methylsulfonylphenyl)-1H-pyrazole;

5-(4-chlorophenyl)-1-(4-methylsulfonylphenyl)-3-(2,4,6-trifluorophenyl)-1H-pyrazole;

5-(4-chlorophenyl)-3-(3,4-dimethoxyphenyl)-1-(4-methylsulfonylphenyl)-1H-pyrazole;

5-(4-chlorophenyl)-3-(3,4-dichlorophenyl)-1-(4-methylsulfonylphenyl)-1H-pyrazole;
3-(2-chlorophenyl)-5-(4-chlorophenyl)-1-(4-methylsulfonylphenyl)-1H-pyrazole;
5-(4-chlorophenyl)-3-(2,4-dichlorophenyl)-1-(4-methylsulfonylphenyl)-1H-pyrazole;
5-(4-chlorophenyl)-3-(3,5-dichlorophenyl)-1-(4-methylsulfonylphenyl)-1H-pyrazole;
5-(4-chlorophenyl)-3-(2,4-dimethoxyphenyl)-1-(4-methylsulfonylphenyl)-1H-pyrazole;
5-(4-chlorophenyl)-3-(2,5-dichlorophenyl)-1-(4-methylsulfonylphenyl)-1H-pyrazole;
5-(4-chlorophenyl)-3-(4-methylphenyl)-1-(4-methylsulfonylphenyl)-1H-pyrazole;
5-(4-chlorophenyl)-3-(3-methylphenyl)-1-(4-methylsulfonylphenyl)-1H-pyrazole;
5-(4-chlorophenyl)-3-(2-methylphenyl)-1-(4-methylsulfonylphenyl)-1H-pyrazole;
5-(4-chlorophenyl)-3-(2,4-dimethylphenyl)-1-(4-methylsulfonylphenyl)-1H-pyrazole;
5-(4-chlorophenyl)-1-(4-methylsulfonylphenyl)-3-(2,4,6-trimethylphenyl)-1H-pyrazole;
5-(4-chlorophenyl)-3-(2,5-dimethylphenyl)-1-(4-methylsulfonylphenyl)-1H-pyrazole;
5-(4-chlorophenyl)-3-(3,5-dimethylphenyl)-1-(4-methylsulfonylphenyl)-1H-pyrazole;
5-(4-chlorophenyl)-3-(2,6-dimethylphenyl)-1-(4-methylsulfonylphenyl)-1H-pyrazole;
5-(4-chlorophenyl)-1-(4-methylsulfonylphenyl)-3-(4-nitrophenyl)-1H-pyrazole;
5-(4-chlorophenyl)-1-(4-methylsulfonylphenyl)-3-(3-nitrophenyl)-1H-pyrazole;
5-(4-chlorophenyl)-1-(4-methylsulfonylphenyl)-3-(2-nitrophenyl)-1H-pyrazole;
5-(4-chlorophenyl)-1-(4-methylsulfonylphenyl)-3-(4-methylthiophenyl)-1H-pyrazole;
5-(4-chlorophenyl)-1-(4-methylsulfonylphenyl)-3-(3-methylthiophenyl)-1H-pyrazole;
5-(4-chlorophenyl)-1-(4-methylsulfonylphenyl)-3-(2-methylthiophenyl)-1H-pyrazole;
5-(4-chlorophenyl)-3-(4-methoxy-2-fluorophenyl)-1-(4-methylsulfonylphenyl)-1H-pyrazole;
5-(4-chlorophenyl)-3-(2-methoxy-4-fluorophenyl)-1-(4-methylsulfonylphenyl)-1H-pyrazole;
3-(4-aminophenyl)-5-(4-chlorophenyl)-1-(4-methylsulfonylphenyl)-1H-pyrazole;
3-(3-aminophenyl)-5-(4-chlorophenyl)-1-(4-methylsulfonylphenyl)-1H-pyrazole;
3-(2-aminophenyl)-5-(4-chlorophenyl)-1-(4-methylsulfonylphenyl)-1H-pyrazole;
5-(4-chlorophenyl)-1-(4-methylsulfonylphenyl)-3-(4-pyridyl)-1H-pyrazole;
5-(4-chlorophenyl)-1-(4-methylsulfonylphenyl)-3-(3-pyridyl)-1H-pyrazole;
5-(4-chlorophenyl)-1-(4-methylsulfonylphenyl)-3-(2-pyridyl)-1H-pyrazole;
5-(4-chlorophenyl)-1-(4-methylsulfonylphenyl)-3-(2-thienyl)-1H-pyrazole;
5-(4-chlorophenyl)-3-(5-chloro-2-thienyl)-1-(4-methylsulfonylphenyl)-1H-pyrazole;
5-(4-chlorophenyl)-1-(4-methylsulfonylphenyl)-3-(3-thienyl)-1H-pyrazole;
5-(4-chlorophenyl)-3-(2-furanyl)-1-(4-methylsulfonylphenyl)-1H-pyrazole;
5-(4-chlorophenyl)-3-(3-furanyl)-1-(4-methylsulfonylphenyl)-1H-pyrazole;
5-(4-chlorophenyl)-1-(4-methylsulfonylphenyl)-3-(4-trifluoromethylphenyl)-1H-pyrazole;
5-(4-chlorophenyl)-1-(4-methylsulfonylphenyl)-3-(3-trifluoromethylphenyl)-1H-pyrazole;
5-(4-chlorophenyl)-1-(4-methylsulfonylphenyl)-3-(2-trifluoromethylphenyl)-1H-pyrazole;
5-(4-chlorophenyl)-3-(4-hydroxyphenyl)-1-(4-methylsulfonylphenyl)-1H-pyrazole;
5-(4-chlorophenyl)-3-(3-hydroxyphenyl)-1-(4-methylsulfonylphenyl)-1H-pyrazole;
5-(4-chlorophenyl)-3-(2-hydroxyphenyl)-1-(4-methylsulfonylphenyl)-1H-pyrazole;
4-[5-(4-chlorophenyl)-1-(4-methylsulfonylphenyl)-1H-pyrazol-3-yl]benzoic acid;
3-[5-(4-chlorophenyl)-1-(4-methylsulfonylphenyl)-1H-pyrazol-3-yl]benzoic acid;
2-[5-(4-chlorophenyl)-1-(4-methylsulfonylphenyl)-1H-pyrazol-3-yl]benzoic acid;
5-(4-chlorophenyl)-3-(4-[N,N-dimethylamino]phenyl)-1-(4-methylsulfonylphenyl)-1H-pyrazole;
5-(4-chlorophenyl)-3-(3-[N,N-dimethylamino]phenyl)-1-(4-methylsulfonylphenyl)-1H-pyrazole;
5-(4-chlorophenyl)-3-(2-[N,N-dimethylamino]phenyl)-1-(4-methylsulfonylphenyl)-1H-pyrazole;
5-(4-chlorophenyl)-3-(4-[N-methylamino]phenyl)-1-(4-methylsulfonylphenyl)-1H-pyrazole;
5-(4-chlorophenyl)-3-(3-[N-methylamino]phenyl)-1-(4-methylsulfonylphenyl)-1H-pyrazole;
5-(4-chlorophenyl)-3-(2-[N-methylamino]phenyl)-1-(4-methylsulfonylphenyl)-1H-pyrazole;
N-[4-[5-(4-chlorophenyl)-1-(4-methylsulfonylphenyl)-1H-pyrazol-3-yl]phenyl]acetamide;
N-[3-[5-(4-chlorophenyl)-1-(4-methylsulfonylphenyl)-1H-pyrazol-3-yl]phenyl]acetamide;
N-[2-[5-(4-chlorophenyl)-1-(4-methylsulfonylphenyl)-1H-pyrazol-3-yl]phenyl]acetamide;
5-(4-chlorophenyl)-3-(4-cyanophenyl)-1-(4-methylsulfonylphenyl)-1H-pyrazole;
5-(4-chlorophenyl)-3-(3-cyanophenyl)-1-(4-methylsulfonylphenyl)-1H-pyrazole;
5-(4-chlorophenyl)-3-(2-cyanophenyl)-1-(4-methylsulfonylphenyl)-1H-pyrazole;
3-(2-bromophenyl)-5-(4-chlorophenyl)-1-(4-methylsulfonylphenyl)-1H-pyrazole;
3-(3-bromophenyl)-5-(4-chlorophenyl)-1-(4-methylsulfonylphenyl)-1H-pyrazole;
3-(4-bromophenyl)-5-(4-chlorophenyl)-1-(4-methylsulfonylphenyl)-1H-pyrazole;
5-(4-chlorophenyl)-3-(4-fluorophenyl)-1-(4-methylsulfonylphenyl)-1H-pyrazole;
5-(4-chlorophenyl)-3-(2,4-difluorophenyl)-1-(4-methylsulfonylphenyl)-1H-pyrazole;
5-(4-chlorophenyl)-3-(2,6-difluorophenyl)-1-(4-methylsulfonylphenyl)-1H-pyrazole;
5-(4-chlorophenyl)-3-(3-fluorophenyl)-1-(4-methylsulfonylphenyl)-1H-pyrazole;
5-(4-chlorophenyl)-1-(4-methylsulfonylphenyl)-3-phenyl-1H-pyrazole;
3-(4-chlorophenyl)-1-(4-methylsulfonylphenyl)-5-(phenyl)-1H-pyrazole;
3-(4-chlorophenyl)-5-(2-fluorophenyl)-1-(4-methylsulfonylphenyl)-1H-pyrazole;
3-(4-chlorophenyl)-5-(3-fluorophenyl)-1-(4-methylsulfonylphenyl)-1H-pyrazole;
3-(4-chlorophenyl)-5-(4-fluorophenyl)-1-(4-methylsulfonylphenyl)-1H-pyrazole;
3-(4-chlorophenyl)-5-(2,4-difluorophenyl)-1-(4-methylsulfonylphenyl)-1H-pyrazole;
3-(4-chlorophenyl)-5-(3,4-difluorophenyl)-1-(4-methylsulfonylphenyl)-1H-pyrazole;

3-(4-chlorophenyl)-5-(2,6-difluorophenyl)-1-(4-methylsulfonylphenyl)-1H-pyrazole;

3-(4-chlorophenyl)-1-(4-methylsulfonylphenyl)-5-(2,4,6-trifluorophenyl)-1H-pyrazole;

3-(4-chlorophenyl)-5-(3,4-difluorophenyl)-1-(4-methylsulfonylphenyl)-1H-pyrazole;

3-(4-chlorophenyl)-5-(2,5-difluorophenyl)-1-(4-methylsulfonylphenyl)-1H-pyrazole;

3-(4-chlorophenyl)-5-(2-chlorophenyl)-1-(4-methylsulfonylphenyl)-1H-pyrazole;

3-(4-chlorophenyl)-5-(3-chlorophenyl)-1-(4-methylsulfonylphenyl)-1H-pyrazole;

3-(4-chlorophenyl)-5-(2,4-dichlorophenyl)-1-(4-methylsulfonylphenyl)-1H-pyrazole;

3-(4-chlorophenyl)-5-(2,5-dichlorophenyl)-1-(4-methylsulfonylphenyl)-1H-pyrazole;

3-(4-chlorophenyl)-5-(2,6-dichlorophenyl)-1-(4-methylsulfonylphenyl)-1H-pyrazole;

3-(4-chlorophenyl)-5-(3,4-dichlorophenyl)-1-(4-methylsulfonylphenyl)-1H-pyrazole;

3-(4-chlorophenyl)-1-(4-methylsulfonylphenyl)-5-(2,4,6-trichlorophenyl)-1H-pyrazole;

3-(4-chlorophenyl)-5-(2-methylphenyl)-1-(4-methylsulfonylphenyl)-1H-pyrazole;

3-(4-chlorophenyl)-5-(3-methylphenyl)-1-(4-methylsulfonylphenyl)-1H-pyrazole;

3-(4-chlorophenyl)-5-(4-methylphenyl)-1-(4-methylsulfonylphenyl)-1H-pyrazole;

3-(4-chlorophenyl)-5-(2,4-dimethylphenyl)-1-(4-methylsulfonylphenyl)-1H-pyrazole;

3-(4-chlorophenyl)-5-(4-[N-methylamino]phenyl)-1-(4-methylsulfonylphenyl)-1H-pyrazole;

3-(4-chlorophenyl)-5-(2-[N-methylamino]phenyl)-1-(4-methylsulfonylphenyl)-1H-pyrazole;

3-(4-chlorophenyl)-5-(3-[N-methylamino]phenyl)-1-(4-methylsulfonylphenyl)-1H-pyrazole;

3-(4-chlorophenyl)-5-(2,5-dimethylphenyl)-1-(4-methylsulfonylphenyl)-1H-pyrazole;

3-(4-chlorophenyl)-5-(2,6-dimethylphenyl)-1-(4-methylsulfonylphenyl)-1H-pyrazole;

3-(4-chlorophenyl)-5-(3,4-dimethylphenyl)-1-(4-methylsulfonylphenyl)-1H-pyrazole;

3-(4-chlorophenyl)-1-(4-methylsulfonylphenyl)-5-(2,4,6-trimethylphenyl)-1H-pyrazole;

3-(4-chlorophenyl)-5-(2-methoxyphenyl)-1-(4-methylsulfonylphenyl)-1H-pyrazole;

3-(4-chlorophenyl)-5-(3-methoxyphenyl)-1-(4-methylsulfonylphenyl)-1H-pyrazole;

3-(4-chlorophenyl)-5-(4-methoxyphenyl)-1-(4-methylsulfonylphenyl)-1H-pyrazole;

3-(4-chlorophenyl)-5-(2,4-dimethoxyphenyl)-1-(4-methylsulfonylphenyl)-1H-pyrazole;

3-(4-chlorophenyl)-5-(2,5-dimethoxyphenyl)-1-(4-methylsulfonylphenyl)-1H-pyrazole;

3-(4-chlorophenyl)-5-(2,6-dimethoxyphenyl)-1-(4-methylsulfonylphenyl)-1H-pyrazole;

3-(4-chlorophenyl)-5-(3,4-dimethoxyphenyl)-1-(4-methylsulfonylphenyl)-1H-pyrazole;

3-(4-chlorophenyl)-1-(4-methylsulfonylphenyl)-5-(2-trifluoromethylphenyl)-1H-pyrazole;

3-(4-chlorophenyl)-1-(4-methylsulfonylphenyl)-5-(3-trifluoromethylphenyl)-1H-pyrazole;

3-(4-chlorophenyl)-1-(4-methylsulfonylphenyl)-5-(4-trifluoromethylphenyl)-1H-pyrazole;

5-(2-aminophenyl)-3-(4-chlorophenyl)-1-(4-methylsulfonylphenyl)-1H-pyrazole;

5-(3-aminophenyl)-3-(4-chlorophenyl)-1-(4-methylsulfonylphenyl)-1H-pyrazole;

5-(4-aminophenyl)-3-(4-chlorophenyl)-1-(4-methylsulfonylphenyl)-1H-pyrazole;

3-(4-chlorophenyl)-5-(2-[N,N-dimethylamino]phenyl)-1-(4-methylsulfonylphenyl)-1H-pyrazole;

3-(4-chlorophenyl)-5-(3-[N,N-dimethylamino]phenyl)-1-(4-methylsulfonylphenyl)-1H-pyrazole;

3-(4-chlorophenyl)-5-(4-[N,N-dimethylamino]phenyl)-1-(4-methylsulfonylphenyl)-1H-pyrazole;

methyl 4-[3-(4-chlorophenyl)-1-(4-methylsulfonylphenyl)-1H-pyrazol-5-yl]benzoate;

methyl 2-[3-(4-chlorophenyl)-1-(4-methylsulfonylphenyl)-1H-pyrazol-5-yl]benzoate;

3-(4-chlorophenyl)-1-(4-methylsulfonylphenyl)-5-(2-nitrophenyl)-1H-pyrazole;

3-(4-chlorophenyl)-1-(4-methylsulfonylphenyl)-5-(3-nitrophenyl)-1H-pyrazole;

3-(4-chlorophenyl)-1-(4-methylsulfonylphenyl)-5-(4-nitrophenyl)-1H-pyrazole;

3-(4-chlorophenyl)-1-(4-methylsulfonylphenyl)-5-(2-methylthiophenyl)-1H-pyrazole;

3-(4-chlorophenyl)-1-(4-methylsulfonylphenyl)-5-(3-methylthiophenyl)-1H-pyrazole;

3-(4-chlorophenyl)-1-(4-methylsulfonylphenyl)-5-(4-methylthiophenyl)-1H-pyrazole;

3-(4-chlorophenyl)-5-(2-cyanophenyl)-1-(4-methylsulfonylphenyl)-1H-pyrazole;

3-(4-chlorophenyl)-5-(3-cyanophenyl)-1-(4-methylsulfonylphenyl)-1H-pyrazole;

3-(4-chlorophenyl)-5-(4-cyanophenyl)-1-(4-methylsulfonylphenyl)-1H-pyrazole;

3-(4-chlorophenyl)-1-(4-methylsulfonylphenyl)-5-(2-thienyl)-1H-pyrazole;

3-(4-chlorophenyl)-1-(4-methylsulfonylphenyl)-5-(3-thienyl)-1H-pyrazole;

3-(4-chlorophenyl)-1-(4-methylsulfonylphenyl)-5-(2-pyridyl)-1H-pyrazole;

3-(4-chlorophenyl)-1-(4-methylsulfonylphenyl)-5-(3-pyridyl)-1H-pyrazole;

3-(4-chlorophenyl)-1-(4-methylsulfonylphenyl)-5-(4-pyridyl)-1H-pyrazole;

3-(4-chlorophenyl)-5-(2-furanyl)-1-(4-methylsulfonylphenyl)-1H-pyrazole;

3-(4-chlorophenyl)-5-(3-furanyl)-1-(4-methylsulfonylphenyl)-1H-pyrazole;

3-(4-chlorophenyl)-5-(2-hydroxyphenyl)-1-(4-methylsulfonylphenyl)-1H-pyrazole;

3-(4-chlorophenyl)-5-(3-hydroxyphenyl)-1-(4-methylsulfonylphenyl)-1H-pyrazole;

3-(4-chlorophenyl)-5-(4-hydroxyphenyl)-1-(4-methylsulfonylphenyl)-1H-pyrazole;

2-[3-(4-chlorophenyl)-1-(4-methylsulfonylphenyl)-1H-pyrazol-5-yl]benzoic acid;

3-[3-(4-chlorophenyl)-1-(4-methylsulfonylphenyl)-1H-pyrazol-5-yl]benzoic acid;

4-[3-(4-chlorophenyl)-1-(4-methylsulfonylphenyl)-1H-pyrazol-5-yl]benzoic acid;

methyl 2-[3-(4-chlorophenyl)-1-(4-methylsulfonylphenyl)-1H-pyrazol-5-yl]benzoate;

methyl 3-[3-(4-chlorophenyl)-1-(4-methylsulfonylphenyl)-1H-pyrazol-5-yl]benzoate;

ethyl 3-[3-(4-chlorophenyl)-1-(4-methylsulfonylphenyl)-1H-pyrazol-5-yl]benzoate;

ethyl 4-[3-(4-chlorophenyl)-1-(4-methylsulfonylphenyl)-1H-pyrazol-5-yl]benzoate;

N-[4-[3-(4-chlorophenyl)-1-(4-methylsulfonylphenyl)-1H-pyrazol-5-yl]phenyl]acetamide;

N-[3-[3-(4-chlorophenyl)-1-(4-methylsulfonylphenyl)-1H-pyrazol-5-yl]phenyl]acetamide;

N-[2-[3-(4-chlorophenyl)-1-(4-methylsulfonylphenyl)-1H-pyrazol-5-yl]phenyl]acetamide;
5-(2-bromophenyl)-3-(4-chlorophenyl)-1-(4-methylsulfonylphenyl)-1H-pyrazole;
5-(3-bromophenyl)-3-(4-chlorophenyl)-1(4-methylsulfonylphenyl)-1H-pyrazole;
5-(4-bromophenyl)-3-(4-chlorophenyl)-1-(4-methylsulfonylphenyl)-1H-pyrazole;
3,5-bis(4-methoxyphenyl)-1-(4- methylsulfonylphenyl)-1H-pyrazole;
3,5-bis(4-methylphenyl)-1-(4- methylsulfonylphenyl)-1H-pyrazole;
3,5-bis(4-nitrophenyl)-1-(4-methylsulfonylphenyl)-1H-pyrazole; 3,5-bis(4-methylthiophenyl)-1-(4-methylsulfonylphenyl)-1H-pyrazole; 3,5-bis(4-aminophenyl)-1-(4-methylsulfonylphenyl)-1H-pyrazole; 3,5-bis(4-trifluoromethylphenyl)-1-(4-methylsulfonylphenyl)-1H-pyrazole;
3,5-bis (4-hydroxyphenyl) -1- (4-methylsulfonylphenyl) -1H-pyrazole;
4,4'-[1-(4-methylsulfonylphenyl)-1H-pyrazol-3,5-diyl] bisbenzoic acid;
3,5-bis(4-cyanophenyl)-1-(4-methylsulfonylphenyl)-1H-pyrazole;
3,5-bis(4-bromophenyl)-1-(4-methylsulfonylphenyl)-1H-pyrazole;
3,5-bis(4-fluorophenyl)-1-(4-methylsulfonylphenyl)-1H-pyrazole;
3,5-bis(phenyl)-4-chloro-1-(4-methylsulfonylphenyl)-1H-pyrazole;
3,5-bis (4-chlorophenyl) -4-methyl-1-(4-methylsulfonylphenyl-1H-pyrazole;
3,5-bis(4-chlorophenyl)-4-ethyl-1-(4-methylsulfonylphenyl-1H-pyrazole;
1-(4-methylsulfonylphenyl)-3,5-bis(4-chlorophenyl)-4-ethyl-1H-pyrazole;
3,5-bis(4-chlorophenyl)-1-(4-methylsulfonylphenyl)-4-propyl-1H-pyrazole;
4-butyl-3,5-bis(4-chlorophenyl)-1-(4-methylsulfonylphenyl)-1H-pyrazole;
3,5-bis(4-chlorophenyl)-4-isopropyl-1-(4-methylsulfonylphenyl)-1H-pyrazole;
3,5-bis(4-chlorophenyl)-1-(4-methylsulfonylphenyl)-4-trifluoromethyl-1H-pyrazole;
3,5-bis(4-chlorophenyl)-4-cyano-1-(4-methylsulfonylphenyl)-1H-pyrazole;
3,5-bis(4-chlorophenyl)-4-difluoromethyl-1-(4-methylsulfonylphenyl)-1H-pyrazole;
3,5-bis(4-chlorophenyl)-1-(4-methylsulfonylphenyl)-1H-pyrazole-4-carboxylic acid;
methyl 3,5-bis(4-chlorophenyl)-1(4-methylsulfonylphenyl)-1H-pyrazole-4-carboxylic acid;
ethyl 3,5-bis(4-chlorophenyl)-1-(4-methylsulfonylphenyl)-1H-pyrazole-4-carboxylic acid;
4-acetyl-3,5-bis(4-chlorophenyl)-1-(4-methylsulfonylphenyl)-1H-pyrazole;
3,5-bis(4-chlorophenyl)-4-formyl-1-(4-methylsulfonylphenyl)-1H-pyrazole;
4-amino-3,5-bis(4-chlorophenyl)-1-(4-methylsulfonylphenyl)-1H-pyrazole;
N-[3,5-bis(4-chlorophenyl)-1-(4-methylsulfonylphenyl)-1H-pyrazol-4-yl]acetamide;
3,5-bis(4-chlorophenyl)-1-(4-methylsulfonylphenyl)-4-(N-[methylsulfonyl])amino-1H-pyrazole;
3,5-bis(4-chlorophenyl)-4-fluoro-1-(4-methylsulfonylphenyl)-1H-pyrazole;
3,5-bis(4-chlorophenyl)-4-chloro-1-(4-methylsulfonylphenyl)-1H-pyrazole; and
3,5-bis(4-chlorophenyl)-4-bromo-1-(4-methylsulfonylphenyl)-1H-pyrazole.

A second more preferred class of compounds consists of those compounds of Formula I wherein $R^1$ is sulfamyl; wherein $R^2$ is aryl or heteroaryl; wherein $R^2$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; wherein $R^3$ is selected from hydrido, lower alkyl, lower haloalkyl, cyano, carboxyl, alkoxycarbonyl, amino, acyl, acylamino, halo and alkylsulfonylamino; wherein $R^4$ is aryl or heteroaryl; wherein $R^4$ is optionally substituted at a substitutable position with one or more radicals selected from halo, lower alkoxy, lower alkyl, nitro, lower alkylthio, amino, lower haloalkyl, hydroxyl, carboxyl, N-monoalkylamino, N,N-dialkylamino, cyano, alkoxycarbonyl and acylamino; provided at least one of $R^2$ and $R^4$ cannot be phenyl or substituted triazole; and further provided $R^2$ cannot be 4-methoxyphenyl or 4-methylphenyl when $R^4$ is 4-methoxyphenyl or 4-methylphenyl; or a pharmaceutically-acceptable salt thereof.

A second class of compounds of particular interest consists of those compounds of Formula I wherein $R^2$ is selected from phenyl, pyrryl, furyl, pyridyl, pyrimidyl, pyrazinyl, pyrazolyl, oxazolyl, isoxazolyl, imidazolyl, thiazyl, pyranyl and thienyl; wherein $R^2$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl and acetamido; wherein $R^3$ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH$—; wherein $R^4$ is selected from phenyl, pyrryl, furyl, pyridyl, pyrimidyl, pyrazinyl, pyrazolyl, oxazolyl, isoxazolyl, imidazolyl, thiazyl, pyranyl and thienyl; wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl and acetamido; or a pharmaceutically-acceptable salt thereof.

A second family of specific compounds of particular interest within Formula I consists of compounds, and pharmaceutically-acceptable salts thereof, as follows:

4-[3,5-bis(4-chlorophenyl)-1H-pyrazol-1-yl]benzenesulfonamide;
4-[5-(4-chlorophenyl)-3-(3,5-difluorophenyl)-1H-pyrazol-1-yl]benzenesulfonamide;
4-[5-(4-chlorophenyl)-3-(2,5-difluorophenyl)-1H-pyrazol-1-yl]benzenesulfonamide;
4-[5-(4-chlorophenyl)3-(3,4-difluorophenyl)-1H-pyrazol-1-yl]benzenesulfonamide;
4-5-(4-chlorophenyl)-[3-(4-methoxyphenyl)-1H-pyrazol-1-yl]benzenesulfonamide;
4-[3-(3-chlorophenyl)-5-(4-chlorophenyl)-1H-pyrazol-1-yl]benzenesulfonamide;
4-[5-(4-chlorophenyl)-3-(2,4,6-trifluorophenyl)-1H-pyrazol-1-yl]benzenesulfonamide;
4-[5-(4-chlorophenyl)-3-(3,4-dimethoxyphenyl)-1H-pyrazol-1-yl]benzenesulfonamide;
4-[5-(4-chlorophenyl)-3-(3,4-dichlorophenyl)-1H-pyrazol-1-yl]benzenesulfonamide;
4-[3-(2-chlorophenyl)-5-(4-chlorophenyl)-1H-pyrazol-1-yl]benzenesulfonamide;
4-[5-(4-chlorophenyl)-3-(2,4-dichlorophenyl)-1H-pyrazol-1-yl]benzenesulfonamide;
4-[5-(4-chlorophenyl)-3-(3,4-dichlorophenyl)-1H-pyrazol-1-yl]benzenesulfonamide;
4-[5-(4-chlorophenyl)-3-(2,4-dimethoxyphenyl)-1H-pyrazol-1-yl]benzenesulfonamide;
4-[5-(4-chlorophenyl)-3-(2,5-dichlorophenyl)-1H-pyrazol-1-yl]benzenesulfonamide;
4-[5-(4-chlorophenyl)-3-(4-methylphenyl)-1H-pyrazol-1-yl]benzenesulfonamide;
4-[5-(4-chlorophenyl)-3-(3-methylphenyl)-1H-pyrazol-1-yl]benzenesulfonamide;
4-[5-(4-chlorophenyl)-3-(2-methylphenyl)-1H-pyrazol-1-yl]benzenesulfonamide;
4-[5-(4-chlorophenyl)-3-(2,4-dimethylphenyl)-1H-pyrazol-1-yl]benzenesulfonamide;
4-[5-(4-chlorophenyl)-3-(2,4,6-trimethylphenyl)-1H-pyrazol-1-yl]benzenesulfonamide;
4-[5-(4-chlorophenyl)-3-(2,5-dimethylphenyl)-1H-pyrazol-1-yl]benzenesulfonamide;
4-[5-(4-chlorophenyl)-3-(3,5-dimethylphenyl)-1H-pyrazol-1-yl]benzenesulfonamide;
4-[5-(4-chlorophenyl)-3-(2,6-dimethylphenyl)-1H-pyrazol-1-yl]benzenesulfonamide;
4-[5-(4-chlorophenyl)-3-(4-nitrophenyl)-1H-pyrazol-1-yl]benzenesulfonamide;
4-[5-(4-chlorophenyl)-3-(3-nitrophenyl)-1H-pyrazol-1-yl]benzenesulfonamide;
4-[5-(4-chlorophenyl)-3-(2-nitrophenyl)-1H-pyrazol-1-yl]benzenesulfonamide;
4-[5-(4-chlorophenyl)-3-(4-methylthiophenyl)-1H-pyrazol-1-yl]benzenesulfonamide;
4-[5-(4-chlorophenyl)-3-(3-methylthiophenyl)-1H-pyrazol-1-yl]benzenesulfonamide;
4-[5-(4-chlorophenyl)-3-(2-methylthiophenyl)-1H-pyrazol-1-yl]benzenesulfonamide;
4-[5-(4-chlorophenyl)-3-(4-methoxy-2-fluorophenyl)-1H-pyrazol-1-yl]benzenesulfonamide;
4-[5-(4-chlorophenyl)-3-(2-methoxy-4-fluorophenyl)-1H-pyrazol-1-yl]benzenesulfonamide;
4-[3-(4-aminophenyl)-5-(4-chlorophenyl)-1H-pyrazol-1-yl]benzenesulfonamide;
4-[3-(3-aminophenyl)-5-(4-chlorophenyl)-1H-pyrazol-1-yl]benzenesulfonamide;
4-[3-(2-aminophenyl)-5-(4-chlorophenyl)-1H-pyrazol-1-yl]benzenesulfonamide;
4-[5-(4-chlorophenyl)-3-(4-pyridyl)-1H-pyrazol-1-yl]benzenesulfonamide;
4-[5-(4-chlorophenyl)-3-(3-pyridyl)-1H-pyrazol-1-yl]benzenesulfonamide;
4-[5-(4-chlorophenyl)-3-(2-pyridyl)-1H-pyrazol-1-yl]benzenesulfonamide;
4-[5-(4-chlorophenyl)-3-(2-thienyl)-1H-pyrazol-1-yl]benzenesulfonamide;
4-[5-(4-chlorophenyl)-3-(5-chloro-2-thienyl)-1H-pyrazol-1-yl]benzenesulfonamide;
4-[5-(4-chlorophenyl)-3-(3-thienyl)-1H-pyrazol-1-yl]benzenesulfonamide;
4-[5-(4-chlorophenyl)-3-(2-furanyl)-1H-pyrazol-1-yl]benzenesulfonamide;
4-[5-(4-chlorophenyl)-3-(3-furanyl)-1H-pyrazol-1-yl]benzenesulfonamide;
4-[5-(4-chlorophenyl)-3-(4-trifluoromethylphenyl)-1H-pyrazol-1-yl]benzenesulfonamide;
4-[5-(4-chlorophenyl)-3-(3-trifluoromethylphenyl)-1H-pyrazol-1-yl]benzenesulfonamide;
4-[5-(4-chlorophenyl)-3-(2-trifluoromethylphenyl)-1H-pyrazol-1-yl]benzenesulfonamide;
4-[5-(4-chlorophenyl)-3-(4-hydroxyphenyl)-1H-pyrazol-1-yl]benzenesulfonamide;
4-[5-(4-chlorophenyl)-3-(3-hydroxyphenyl)-1H-pyrazol-1-yl]benzenesulfonamide;
4-[5-(4-chlorophenyl)-3-(2-hydroxyphenyl)-1H-pyrazol-1-yl]benzenesulfonamide;
4-[1-(4-aminosulfonylphenyl)-5-(4-chlorophenyl)-1H-pyrazol-3-yl]benzoic acid;
2-[1-(4-aminosulfonylphenyl)-5-(4-chlorophenyl)-1H-pyrazol-3-yl]benzoic acid;
3-[1-(4-aminosulfonylphenyl)-5-(4-chlorophenyl)-1H-pyrazol-3-yl]benzoic acid;
4-[5-(4-chlorophenyl)-3-(4-[N,N-dimethylamino]phenyl)-1H-pyrazol-1-yl]benzenesulfonamide;
4-[5-(4-chlorophenyl)-3-(3-[N,N-dimethylamino]phenyl)-1H-pyrazol-1-yl]benzenesulfonamide;
4-[5-(4-chlorophenyl)-3-(2-[N,N-dimethylamino]phenyl)-1H-pyrazol-1-yl]benzenesulfonamide;
4-[5-(4-chlorophenyl)-3-(4-[N-methylamino]phenyl)-1H-pyrazol-1-yl]benzenesulfonamide;
4-[5-(4-chlorophenyl)-3-(3-[N-methylamino]phenyl)-1H-pyrazol-1-yl]benzenesulfonamide;
4-[5-(4-chlorophenyl)-3-(2-[N-methylamino]phenyl)-1H-pyrazol-1-yl]benzenesulfonamide;
N-[4-[1-(4-aminosulfonylphenyl)-5-(4-chlorophenyl)-1H-pyrazol-3-yl]phenyl]acetamide;
N-[3-[1-(4-aminosulfonylphenyl)-5-(4-chlorophenyl)-1H-pyrazol-3-yl]phenyl]acetamide;
N-[2-[1-(4-aminosulfonylphenyl)-5-(4-chlorophenyl)-1H-pyrazol-3-yl]phenyl]acetamide;
4-[5-(4-chlorophenyl)-3-(4-cyanophenyl)-1H-pyrazol-1-yl]benzenesulfonamide;
4-[5-(4-chlorophenyl)-3-(3-cyanophenyl)-1H-pyrazol-1-yl]benzenesulfonamide;
4-[5-(4-chlorophenyl)-3-(2-cyanophenyl)-1H-pyrazol-1-yl]benzenesulfonamide;

4-[3-(2-bromophenyl)-5-(4-chlorophenyl)-1H-pyrazol-1-yl]
benzenesulfonamide;
4-[3-(3-bromophenyl)-5-(4-chlorophenyl)-1H-pyrazol-1-yl]
benzenesulfonamide;
4-[3-(4-bromophenyl)-5-(4-chlorophenyl)-1H-pyrazol-1-yl]
benzenesulfonamide;
4-[5-(4-chlorophenyl)-3-(4-fluorophenyl)-1H-pyrazol-1-yl]
benzenesulfonamide;
4-[5-(4-chlorophenyl)-3-(2,4-difluorophenyl)-1H-pyrazol-
1-yl]benzenesulfonamide;
4-[5-(4-chlorophenyl)-3-(2,6-difluorophenyl)-1H-pyrazol-
1-yl]benzenesulfonamide;
4-[5-(4-chlorophenyl)-3-(3-fluorophenyl)-1H-pyrazol-1-yl]
benzenesulfonamide;
4-[3-(4-chlorophenyl)-5-(2-fluorophenyl)-1H-pyrazol-1-yl]
benzenesulfonamide;
4-[3-(4-chlorophenyl)-5-(3-fluorophenyl)-1H-pyrazol-1-yl]
benzenesulfonamide;
4-[3-(4-chlorophenyl)-5-(4-fluorophenyl)-1H-pyrazol-1-yl]
benzenesulfonamide;
4-[3-(4-chlorophenyl)-5-(2,4-difluorophenyl)-1H-pyrazol-
1-yl]benzenesulfonamide;
4-[3-(4-chlorophenyl)-5-(2,6-difluorophenyl)-1H-pyrazol-
1-yl]benzenesulfonamide;
4-[3-(4-chlorophenyl)-5-(2,4,6-trifluorophenyl)-1H-
pyrazol-1-yl]benzenesulfonamide;
4-[3-(4-chlorophenyl)-5-(3,4-difluorophenyl)-1H-pyrazol-
1-yl]benzenesulfonamide;
4-[3-(4-chlorophenyl)-5-(2,5 difluorophenyl)-1H-pyrazol-
1-yl]benzenesulfonamide;
4-[3-(4-chlorophenyl)-5-(2-chlorophenyl)-1H-pyrazol-1-yl]
benzenesulfonamide;
4-[3-(4-chlorophenyl)-5-(3-chlorophenyl)-1H-pyrazol-1-yl]
benzenesulfonamide;
4-[3-(4-chlorophenyl)-5-(2,4-dichlorophenyl)-1H-pyrazol-
1-yl]benzenesulfonamide;
4-[3-(4-chlorophenyl)-5-(2,5-dichlorophenyl)-1H-pyrazol-
1-yl]benzenesulfonamide;
4-[3-(4-chlorophenyl)-5-(2,6-dichlorophenyl)-1H-pyrazol-
1-yl]benzenesulfonamide;
4-[3-(4-chlorophenyl)-5-(3,4-dichlorophenyl)-1H-pyrazol-
1-yl]benzenesulfonamide;
4-[3-(4-chlorophenyl)-5-(2,4,6-trichlorophenyl)-1H-
pyrazol-1-yl]benzenesulfonamide;
4-[3-(4-chlorophenyl)-5-(2-methylphenyl)-1H-pyrazol-1-
yl]benzenesulfonamide;
4-[3-(4-chlorophenyl)-5-(3-methylphenyl)-1H-pyrazol-1-
yl]benzenesulfonamide;
4-[3-(4-chlorophenyl)-5-(4-methylphenyl)-1H-pyrazol-1-
yl]benzenesulfonamide;
4-[3-(4-chlorophenyl)-5-(2,4-dimethylphenyl)-1H-pyrazol-
1-yl]benzenesulfonamide;
4-(3-(4-chlorophenyl)-5-(4-[N-methylamino]phenyl)-1H-
pyrazol-1-yl]benzenesulfonamide;
4-[3-(4-chlorophenyl)-5-(2-[N-methylamino]phenyl)-1H-
pyrazol-1-yl]benzenesulfonamide;
4-[3-(4-chlorophenyl)-5-(3-[N-methylamino]phenyl)-1H-
pyrazol-1-yl]benzenesulfonamide;
4-[3-(4-chlorophenyl)-5-(3,4-difluorophenyl)-1H-pyrazol-
1-yl]benzenesulfonamide;
4-[3-(4-chlorophenyl)-5-(2,5-dimethylphenyl)-1H-pyrazol-
1-yl]benzenesulfonamide;
4-[3-(4-chlorophenyl)-5-(2,6-dimethylphenyl)-1H-pyrazol-
1-yl]benzenesulfonamide;
4-[3-(4-chlorophenyl)-5-(3,4-dimethylphenyl)-1H-pyrazol-
1-yl]benzenesulfonamide;
4-[3-(4-chlorophenyl)-5-(2,4,6-trimethylphenyl)-1H-
pyrazol-1-yl]benzenesulfonamide;

4-[3-(4-chlorophenyl)-5-(2-methoxyphenyl)-1H-pyrazol-1-
yl]benzenesulfonamide;
4-[3-(4-chlorophenyl)-5-(3-methoxyphenyl)-1H-pyrazol-1-
yl]benzenesulfonamide;
4-[3-(4-chlorophenyl)-5-(4-methoxyphenyl)-1H-pyrazol-1-
yl]benzenesulfonamide;
4-[3-(4-chlorophenyl)-5-(2,4-dimethoxyphenyl)-1H-
pyrazol-1-yl]benzenesulfonamide;
4-[3-(4-chlorophenyl)-5-(2,5-dimethoxyphenyl)-1H-
pyrazol-1-yl]benzenesulfonamide;
4-[3-(4-chlorophenyl)-5-(2,6-dimethoxyphenyl)-1H-
pyrazol-1-yl]benzenesulfonamide;
4-[3-(4-chlorophenyl)-5-(3,4-dimethoxyphenyl)-1H-
pyrazol-1-yl]benzenesulfonamide;
4-[3-(4-chlorophenyl)-5-(2-trifluoromethylphenyl)-1H-
pyrazol-1-yl]benzenesulfonamide;
4-[3-(4-chlorophenyl)-5-(3-trifluoromethylphenyl)-1H-
pyrazol-1-yl]benzenesulfonamide;
4-[3-(4-chlorophenyl)-5-(4-trifluoromethylphenyl)-1H-
pyrazol-1-yl]benzenesulfonamide;
4-[5-(2-aminophenyl)-3-(4-chlorophenyl)-1H-pyrazol-1-yl]
benzenesulfonamide;
4-[5-(3-aminophenyl)-3-(4-chlorophenyl)-1H-pyrazol-1-yl]
benzenesulfonamide;
4-[5-(4-aminophenyl)-3-(4-chlorophenyl)-1H-pyrazol-1-yl]
benzenesulfonamide;
4-[3-(4-chlorophenyl)-5-(2-[N,N-dimethylamino]phenyl)-
1H-pyrazol-1-yl]benzenesulfonamide;
4-[3-(4-chlorophenyl)-5-(3-[N,N-dimethylamino]phenyl)-
1H-pyrazol-1-yl]benzenesulfonamide;
4-[3-(4-chlorophenyl)-5-(4-[N,N-dimethylamino]phenyl)-
1H-pyrazol-1-yl]benzenesulfonamide;
methyl 4-[1-(4-aminosulfonylphenyl)-5-(4-chlorophenyl)-
1H-pyrazol-3-yl]benzoate;
methyl 2-[1-(4-aminosulfonylphenyl)-5-(4-chlorophenyl)-
1H-pyrazol-3-yl]benzoate;
methyl 3-[1-(4-aminosulfonylphenyl)-5-(4-chlorophenyl)-
1H-pyrazol-3-yl]benzoate;
4-[3-(4-chlorophenyl)-5-(2-nitrophenyl)-1H-pyrazol-1-yl]
benzenesulfonamide;
4-[3-(4-chlorophenyl)-5-(3-nitrophenyl)-1H-pyrazol-1-yl]
benzenesulfonamide;
4-[3-(4-chlorophenyl)-5-(4-nitrophenyl)-1H-pyrazol-1-yl]
benzenesulfonamide;
4-[3-(4-chlorophenyl)-5-(2-methylthiophenyl)-1H-pyrazol-
1-yl]benzenesulfonamide;
4-[3-(4-chlorophenyl)-5-(3-methylthiophenyl)-1H-pyrazol-
1-yl]benzenesulfonamide;
4-[3-(4-chlorophenyl)-5-(4-methylthiophenyl)-1H-pyrazol-
1-yl]benzenesulfonamide;
4-[3-(4-chlorophenyl)-5-(2-cyanophenyl)-1H-pyrazol-1-yl]
benzenesulfonamide;
4-[3-(4-chlorophenyl)-5-(3-cyanophenyl)-1H-pyrazol-1-yl]
benzenesulfonamide;
4-[3-(4-chlorophenyl)-5-(4-cyanophenyl)-1H-pyrazol-1-yl]
benzenesulfonamide;
4-[3-(4-chlorophenyl)-5-(2-thienyl)-1H-pyrazol-1-yl]
benzenesulfonamide;
4-[3-(4-chlorophenyl)-5-(5-chloro-2-thienyl)-1H-pyrazol-1-
yl]benzenesulfonamide;
4-[3-(4-chlorophenyl)-5-(3-thienyl)-1H-pyrazol-1-yl]
benzenesulfonamide;
4-[3-(4-chlorophenyl)-5-(2-pyridyl)-1H-pyrazol-1-yl]
benzenesulfonamide;
4-[3-(4-chlorophenyl)-5-(3-pyridyl)-1H-pyrazol-1-yl]
benzenesulfonamide;
4-[3-(4-chlorophenyl)-5-(4-pyridyl)-1H-pyrazol-1-yl]
benzenesulfonamide;

4-[3-(4-chlorophenyl)-5-(2-furanyl)-1H-pyrazol-1-yl]
benzenesulfonamide;
4-[3-(4-chlorophenyl)-5-(3-furanyl)-1H-pyrazol-1-yl]
benzenesulfonamide;
4-[3-(4-chlorophenyl)-5-(2-hydroxyphenyl)-1H-pyrazol-1-yl]benzenesulfonamide;
4-[3-(4-chlorophenyl)-5-(3-hydroxyphenyl)-1H-pyrazol-1-yl]benzenesulfonamide;
4-[3-(4-chlorophenyl)-5-(4-hydroxyphenyl)-1H-pyrazol-1-yl]benzenesulfonamide;
2-[1-(4-aminosulfonylphenyl)-3-(4-chlorophenyl)-1H-pyrazol-5-yl]benzoic acid;
3-[1-(4-aminosulfonylphenyl)-3-(4-chlorophenyl)-1H-pyrazol-5-yl]benzoic acid;
4-[1-(4-aminosulfonylphenyl)-3-(4-chlorophenyl)-1H-pyrazol-5-yl]benzoic acid;
ethyl [3-[1-(4-aminosulfonylphenyl)-3-(4-chlorophenyl)-1H-pyrazol-5-yl]]benzoate;
ethyl [4-[1-(4-aminosulfonylphenyl)-3-(4-chlorophenyl)-1H-pyrazol-5-yl]]benzoate;
N-[4-[1-(4-aminosulfonylphenyl)-3-(4-chlorophenyl)-1H-pyrazol-5-yl]phenyl]acetamide;
N-[3-[1-(4-aminosulfonylphenyl)-3-(4-chlorophenyl)-1H-pyrazol-5-yl]phenyl]acetamide;
N-[2-[1-(4-aminosulfonylphenyl)-3-(4-chlorophenyl)-1H-pyrazol-5-yl]phenyl]acetamide;
4-[5-(2-bromophenyl)-3-(4-chlorophenyl)-1H-pyrazol-1-yl]
benzenesulfonamide;
4-[5-(3-bromophenyl)-3-(4-chlorophenyl)-1H-pyrazol-1-yl]
benzenesulfonamide;
4-[5-(4-bromophenyl)-3-(4-chlorophenyl)-1H-pyrazol-1-yl]
benzenesulfonamide;
4-[3,5-bis(4-methoxyphenyl)-1H-pyrazol-1-yl]
benzenesulfonamide;
4-[3,5-bis(4-methylphenyl)-1H-pyrazol-1-yl]
benzenesulfonamide;
4-[3,5-bis(4-nitrophenyl)-1H-pyrazol-1-yl]
benzenesulfonamide;
4-[3,5-bis(4-methylthiophenyl)-1H-pyrazol-1-yl]
benzenesulfonamide;
4-[3,5-bis(4-aminophenyl)-1H-pyrazol-1-yl]
benzenesulfonamide;
4-[3,5-bis(4-trifluoromethylphenyl)-1H-pyrazol-1-yl]
benzenesulfonamide;
4-[3,5-bis(4-hydroxyphenyl)-1H-pyrazol-1-yl]
benzenesulfonamide;
4,4'-[1-(4-aminosulfonylphenyl)-1H-pyrazol-3,5-diyl]
bisbenzoic acid;
4-[3,5-bis(4-cyanophenyl)--1H-pyrazol-1-yl]
benzenesulfonamide;
4-[3,5-bis(4-bromophenyl)-1H-pyrazol-1-yl]
benzenesulfonamide;
4-[3,5-bis(4-fluorophenyl)-1H-pyrazol-1-yl]
benzenesulfonamide;
4-[3,5-bis(4-chlorophenyl)-4-methyl-1H-pyrazol-1-yl]
benzenesulfonamide;
4-[3,5-bis(4-chlorophenyl)-4-ethyl-1H-pyrazol-1-yl]
benzenesulfonamide;
4-[3,5-bis(4-chlorophenyl)-4-propyl-1H-pyrazol-1-yl]
benzenesulfonamide;
4-[3,5-bis(4-chlorophenyl)-4-butyl-1H-pyrazol-1-yl]
benzenesulfonamide;
4-[3,5-bis(4-chlorophenyl)-$^4$-isopropyl-1H-pyrazol-1-yl]
benzenesulfonamide;
4-[3,5-bis(4-chlorophenyl)-4-(trifluoromethyl)-1H-pyrazol-1-yl]benzenesulfonamide;
4-[3,5-bis(4-chlorophenyl)-4-cyano-1H-pyrazol-1-yl]
benzenesulfonamide;
4-[3,5-bis(4-chlorophenyl)-4-(difluoromethyl)-1H-pyrazol-1-yl]benzenesulfonamide;
1-(4-aminosulfonylphenyl)-3,5-bis(4-chlorophenyl)-1H-1-pyrazole-4-carboxylic acid;
methyl 1-(4-aminosulfonylphenyl)-3,5-bis(4-chlorophenyl)-1H-pyrazole-4-carboxylate;
ethyl 1-(4-aminosulfonylphenyl)-3,5-bis(4-chlorophenyl)-1H-pyrazole-4-carboxylate;
4-[4-acetyl-3,5-bis(4-chlorophenyl)-1H-pyrazol-1-yl]
benzenesulfonamide;
4-[3,5-bis(4-chlorophenyl)-4-formyl-1H-pyrazol-1-yl]
benzenesulfonamide;
4-[4-amino-3,5-bis(4-chlorophenyl)-1H-pyrazol-1-yl]
benzenesulfonamide;
N-[1-(4-aminosulfonylphenyl)-3,5-bis(4-chlorophenyl)-1H-pyrazol-4-yl]acetamide;
4-[3,5-bis(4-chlorophenyl)-4-(N-[methylsulfonyl])amino-1H-pyrazol-1-yl]benzenesulfonamide;
4-[3,5-bis(4-chlorophenyl)-4-fluoro-1H-pyrazol-1-yl]
benzenesulfonamide;
4-[3,5-bis(phenyl)-4-chloro-1H-pyrazol-1-yl]
benzenesulfonamide; and
4-[3,5-bis(4-chlorophenyl)-4-chloro-1H-pyrazol-1-yl]
benzenesulfonamide; and
4-[4-bromo-3,5-bis(4-chlorophenyl)-1H-pyrazol-1-yl]
benzenesulfonamide.

Where the term "alkyl" is used, either alone or within other terms such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl, and the like. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocyclic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. Examples of preferred "heteroaryl" radicals include five or six membered heteroaryl, where the heteroatoms may be selected from nitrogen, sulfur and oxygen, including thienyl, pyrryl, furyl, pyridyl, pyrimidyl, pyrazinyl, pyrazolyl, oxazolyl, isoxazolyl, imidazolyl, thiazolyl, pyranyl and tetrazolyl. The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "halo" means halogens such as fluorine, chlorine, bromine or iodine atoms. The term "hydrido" denotes a single hydrogen atom (H). This hydrido radical may be attached, for example, to an oxygen atom to form a hydroxyl group or two hydrido radicals may be attached to a carbon atom to form a methylene ($-CH_2$) radical. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two of the same halo atoms or a combination of different halo radicals and polyhaloalkyl radicals may have more than two of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "sulfonyl", whether used alone or linked to other terms such as "alkylsulfonyl", denotes respectively divalent radicals $-SO_2-$. "Alkylsulfonyl", embraces alkyl radicals attached to a sulfonyl radical, where alkyl is defined as above. The terms "aminosulfonyl", "sulfamyl" and "sulfonamidyl" denote a sulfonyl radical substituted with an amine radical, forming a sulfonamide ($-SO_2NH_2$). The terms "carboxy" or "carboxyl" denotes $-CO_2H$. The term "carbonyl", whether used alone or with other terms, such as "alkylcarbonyl", denotes $-(C=O)-$. The term "alkoxycarbonyl" means a radical containing an alkoxy radical, as defined above, attached via an oxygen atom to a carbonyl radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The terms "N-alkylamino" and "N,N-dialkylamino" denote amino radicals which have been substituted with one alkyl radical and with two alkyl radicals, respectively. The term "acyl", whether used alone, or within a term such as "acylamino", denotes a radical provided by a residue after removal of hydroxyl from an organic acid. The term "acylamino" embraces an amino radical substituted with an acyl radical. An example of an "acylamino" radical is the acetylamino or acetamido radical ($CH_3C(=O)-NH-$). The term "alkylsulfonylamino" denotes an amino radical substituted with an alkylsulfonyl radical as defined above. An example of an "alkylsulfonylamino" radical is methylsulfonylamino ($CH_3SO_2NH-$).

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I.

Also included in the family of compounds of Formula I are the pharmaceutically-acceptable salts thereof. The term "pharmaceutically-acceptable salts", embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL METHOD OF SYNTHESIS

The compounds of the invention can be synthesized according to the following procedures of Schemes I–IV, wherein the $R^1$–$R^4$ substituents are as defined for Formula I, above, except where further noted.

SCHEME I

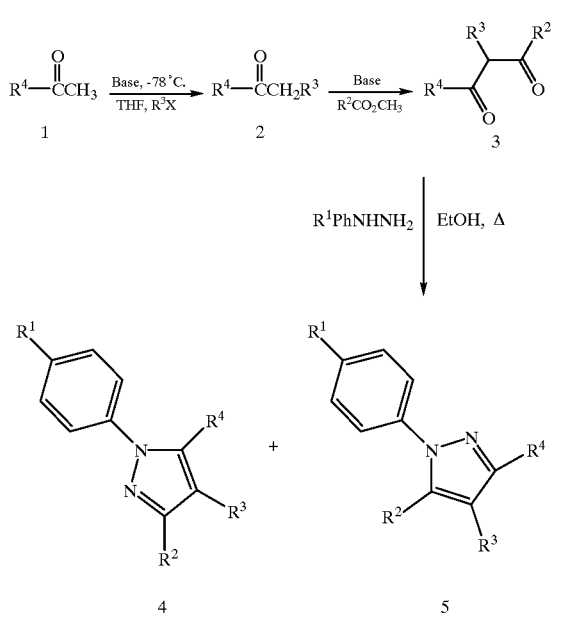

Synthetic Scheme I shows the preparation of tetrasubstituted pyrazoles from starting material 1. In step 1 of synthetic Scheme I, the phenyl-methyl ketone 1 is treated with a base (such as lithium diisopropylamide or LiHMDS) and an alkylating reagent ($R^3X$, where X represents a leaving group such as tosyl) to give the substituted ketone 2. In step 2, the substituted ketone 2 is treated with base, such as sodium methoxide, and an ester to give the intermediate diketone 3 in a procedure similar to that developed by Reid and Calvin, *J. Amer. Chem. Soc.*, 72, 2948–2952 (1950). When $R^3$ is alkyl, a strong base, such as LiHMDS, and an ester equivalent (an activated ester or anhydride) may be used. In step 3, the diketone 3 is reacted with a substituted phenylhydrazine in acetic acid or an alcoholic solvent to give a mixture of pyrazoles 4 and 5. Purification of the desired pyrazole 4 can be achieved by chromatography or recrystallization.

SCHEME II

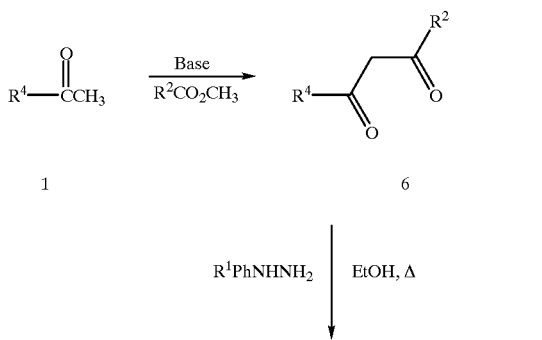

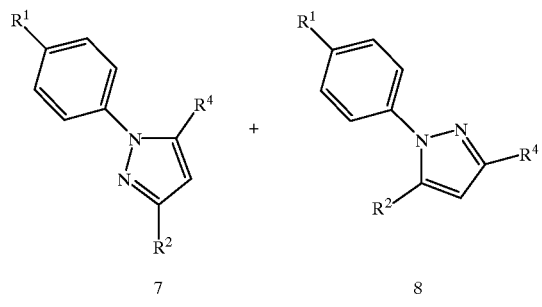

Synthetic Scheme II shows the preparation of compounds embraced by Formula I, where $R^3$ is a hydrogen atom. In step 1, ketone 1 is treated with a base, preferably NaOMe or NaH, and an ester, or ester equivalent, to form the intermediate diketone 6 which is used without further purification. In step 2, diketone 6 in an anhydrous aprotic solvent, such as absolute ethanol or acetic acid, is treated with the free base or the hydrochloride salt of a phenylhydrazine at reflux for 24 hours to afford a mixture of pyrazoles 7 and 8. Recrystallization from diethyl ether/hexane or chromatography affords 7, usually as a light yellow or tan solid.

EXAMPLE 1

Scheme III

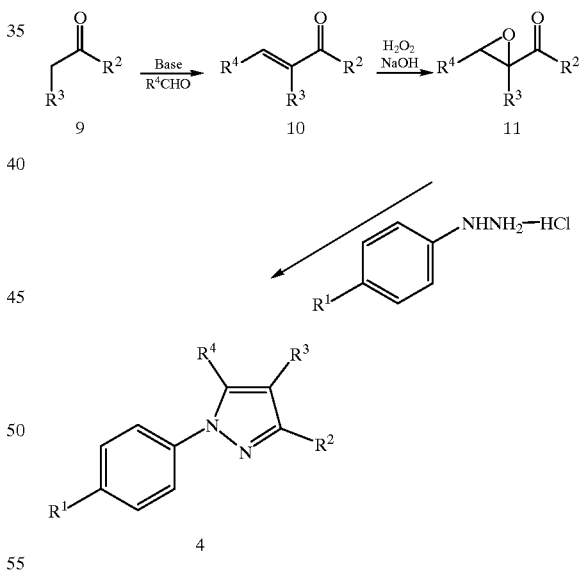

Synthetic Scheme III shows a regioselective preparation of substituted pyrazoles 4 of the present invention from ketones 9. Commercially available chalcones 10 or their heterocyclic analogs are epoxidized, preferably with basic hydrogen peroxide to give epoxyketones 11, which are treated with 4-sulfonamidophenylhydrazine hydrochloride to provide a single pyrazole 4. In cases where the starting chalcones 10 are not available, they can be synthesized from a ketone 9 and an aldehyde in the presence of base.

Scheme IV

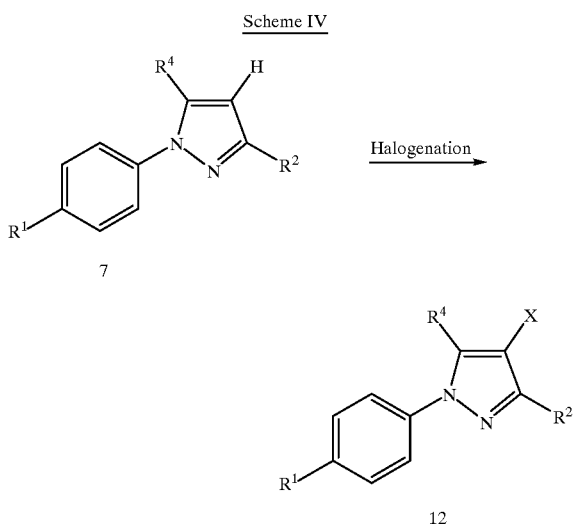

Synthetic Scheme IV shows the preparation of pyrazoles 12 halogenated at position 4. Treatment of the triarylpyrazole 7 (where R=H) with a halogenating reagent, preferably sulfuryl chloride, provides the 4-halo-1,3,5-triarylpyrazole 12.

The following examples contain detailed descriptions of the methods of preparation of compounds of Formula I. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

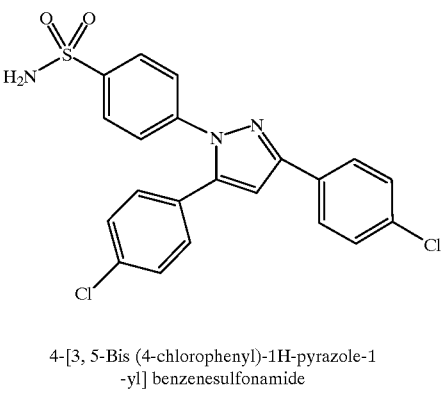

4-[3, 5-Bis (4-chlorophenyl)-1H-pyrazole-1
-yl] benzenesulfonamide

Step 1. Preparation of 1,3-bis[4-(chloro)phenyl]-1,3-diketopropane.

A 250 mL round bottomed flask equipped with reflux condenser and provisions for magnetic stirring was charged with methyl 4-chlorobenzoate (6.07 g, 35.6 mmol), 4'-chloroacetophenone (5.0 g, 32.3 mmol) and THF (100 mL). Sodium methoxide (25% in methanol, 10.5 mL) was added in one portion. The reaction was stirred at room temperature for 6 hours and heated to reflux for 16 hours. The reaction mixture was cooled to room temperature and diluted with hydrochloric acid (1N, 40 mL). Upon cooling to 0° C. crystals formed that were isolated by filtration, washed with cold water and air dried to afford 6.32 g (67%) of pure diketone suitable for use in the next step: $^1$H NMR (CDCl$_3$/300 MHz) 7.91 (d, J=8.66 Hz, 4H), 7.46 (d, J=8.66 Hz, 4H), 6.77 (s, 1H).

Step 2. Preparation of 4-[3,5-bis(4-[chlorolphenyl)-1H-pyrazole-1-yl]benzenesulfonamide.

A 100 mL round-bottomed flask equipped with magnetic stirrer and nitrogen inlet was charged with 1,3-bis[4-(chloro)phenyl]-1,3-diketopropane from Step 1 (2.0 g, 6.82 mmol), 4-sulfonamidylphenylhydrazine hydrochloride (1.68 g, 7.51 mmol) and glacial acetic acid (30 mL). The reaction mixture was heated to reflux for 16 hours. After cooling to room temperature, the reaction mixture was diluted water until the solution became cloudy (25 mL) and cooled to 0° C. for 0.5 hour whereupon a solid formed that was isolated by filtration and air dried to afford 2.42 g (80%) of crude product. The crude product was washed with dichloromethane to yield 1.56 g (51%) of pure 4-[3,5-bis(4-chlorophenyl)-1H-pyrazol-1-yl]benzenesulfonamide: $^1$H NMR (DMSO/300 MHz) 7.94 (d, J=8.66 Hz, 2H), 7.85 (d, J=8.66 Hz, 2H), 7.54–7.32 (m, 8H), 7.28 (s, 1H), 7.03 (s, 1H). Mass spectrum, MH+=445. Elemental analysis calc'd for C$_{21}$H$_{15}$N$_3$O$_2$Cl$_2$S: C, 56.77; H, 3.40; N, 9.46; Cl, 15.96; S, 7.22. Found: C, 56.50; H, 3.48; N, 9.21; Cl, 15.76; S, 7.41.

EXAMPLE 2

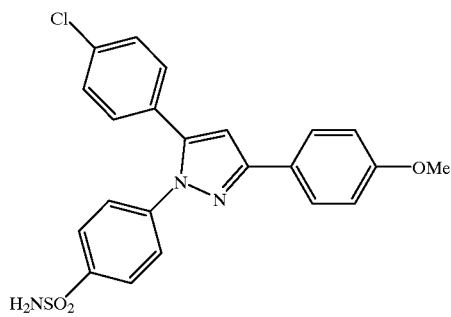

4-(5-(4-Chlorophenyl)-3-(4-methoxyphenyl)-1H-pyrazol-1-yl) benzenesulfonamide

Step 1: Preparation of 3-(4-chlorophenyl)-2,3-epoxy-4'-methoxypropiophenone

A hot solution of 4-chloro-4'-methoxychalcone in ethanol (15 mL) and acetone (5 mL) was cooled to 50° C. and treated with hydrogen peroxide (30%, 2 mL) and 4N NaOH (1.5 mL). The resulting precipitate was filtered and dried in vacuo to obtain 1.3 g of a white crystalline solid: Anal. calc'd for C$_{16}$H$_{13}$ClO$_3$·0.5 H$_2$O: C, 64.55; H, 4.74. Found: C, 64.68; H, 4.42.

Step 2: Preparation of 4-(5-(4-chlorophenyl)-3-(4-methoxyphenyl)-1H-prazol-1-yl)benzenesulfonamide The epoxide from Step 1 (500 mg) and 4-sulfonamidophenylhydrazine hydrochloride (390 mg) in ethanol (5 mL) and 3 drops of acetic acid were stirred at reflux for 3 hours. The reaction mixture was partitioned between water (50 mL) and ethyl acetate (100 mL). The aqueous was extracted with ethyl acetate (3×) and the combined extracts dried (MgSO$_4$) and concentrated. The crude product was chromatographed on silica gel with 30:70 ethyl acetate/hexane as eluent to obtain 198 mg of the desired product: Anal. calc'd for C$_{22}$H$_{18}$ClN$_3$O$_3$S: C, 60.07; H, 4.12; N, 9.55. Found: C, 59.87; H, 4.09; N, 9.52.

The following compounds were prepared from commercially available chalcones or heterocyclic analogs as described in Example 2:

(2a) 4-(3,5-bis(4-methylphenyl)-1H-pyrazol-1-yl)benzenesulfonamide: White solid: Anal. calc'd for $C_{23}H_{21}N_3O_2S$: C, 68.46; H, 5.25; N, 10.41. Found: C, 68.06; H, 5.02; N, 10.38.

(2b) 4-(5-(4-chlorophenyl)-3-phenyl-1H-pyrazol-1-yl)benzenesulfonamide: Yellow solid: Anal. calc'd for $C_{21}H_{16}ClN_3O_2S.0.1H_2O$: C, 61.27; H, 3.97; N, 10.21. Found: C, 61.01; H, 4.04; N, 9.90.

(2c) 4-(3,5-bis(4-methoxyphenyl)-1H-pyrazol-1-yl)benzenesulfonamide: Light yellow solid: Anal. calc'd for $C_{23}H_{21}N_3O_4S.0.3\ H_2O$: C, 62.66; H, 4.94; N, 9.53. Found: C, 62.30; H, 4.80; N, 9.20.

(2d) 4-(5-(4-chlorophenyl)-3-(4-methylphenyl)-1H-pyrazol-1-yl)benzenesulfonamide: Yellow solid: Anal. calc'd for $C_{22}H_{18}ClN_3O_2S.0.2\ H_2O$: C, 61.81; H, 4.34; N, 9.83. Found: C, 61.63; H, 4.31; N, 9.56.

(2e) 4-(5-(4-chlorophenyl)-3-(4-nitrophenyl)-1H-pyrazol-1-yl)benzenesulfonamide: Yellow solid: Anal. calc'd for $C_{21}H_{15}ClN_4O_4S.0.6\ H_2O$: C, 54.16; H, 3.51; N, 12.03. Found: C, 54.24; H, 3.23; N, 11.65.

(2f) 4-(5-(4-chlorophenyl)-3-(2-furyl)-1H-pyrazol-1-yl)benzenesulfonamide: Anal. calc'd for $C_{19}H_{14}ClN_3O_3S$: C, 57.07; H, 3.53; N, 10.51; Cl, 8.87. Found: C, 56.86; H, 3.21; N, 10.52; Cl, 8.76.

(2 g) 4-(5-(4-chlorophenyl)-3-(5-chloro-2-thienyl)-1H-pyrazol-1-yl)benzenesulfonamide: Anal. calc'd for $C_{19}H_{13}Cl_2N_3O_2S_2$: C, 50.67; H, 2.91; N,9.33. Found: C, 50.55; H, 2.84; N, 9.02.

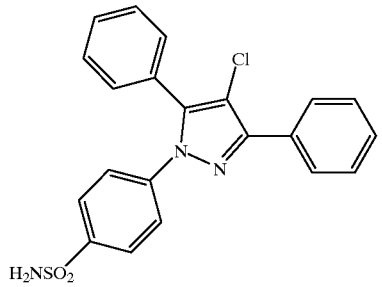

4-(4-chloro-3, 5-diphenyl-1H-pyrazol-1-yl) benzenesulfonamide

Step 1: Preparation of 4-(3,5-diphenyl-1H-pyrazol-1-yl)benzenesulfonamide

Dibenzoylmethane (2.0 g, 8.9 mmol) and 4-sulfonamidophenylhydrazine hydrochloride (2 g) were stirred in 20 mL ethanol at reflux for 3 hours and the mixture cooled and poured into 200 mL water. The solid was filtered, dissolved in ethyl acetate, dried over $MgSO_4$, filtered and concentrated. Flash chromatography using 40:60 ethyl acetate/hexane provided the desired compound (1.3 g).

Step 2: Preparation of 4-(4-chloro-3,5-diphenyl-1H-pyrazol-1-yl)benzenesulfonamide To the pyrazole prepared in Step 1 (150 mg) in 10 ml of methylene chloride was added sulfuryl chloride (1 mL) dropwise at room temperature. The reaction mixture was then stirred at room temperature for 2 hours and quenched with water (10 mL) and extracted with ethyl acetate (3×). The combined extracts were dried over $MgSO_4$ and concentrated. Recrystallization from ethyl acetate furnished a white solid: Anal. calc'd for $C_{21}H_{16}N_3ClSO_2$: C, 61.54; H, 3.93; N, 10.25. Found: C, 61.30; H, 3.74; N, 10.02.

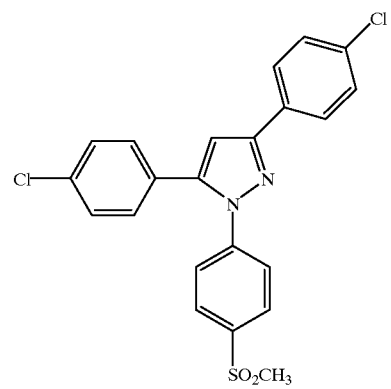

1-[4-(Methylsulfonyl) phenyl]-3, 5-bis (4-chlorophenyl)-1H-pyrazole

Step 1: Preparation of 1,3-[4-chlorophenyl]-propane-1,3-dione

Methyl-(4-chlorobenzoate) (8.20 g, 48 mmol) was placed in a 500 mL three-necked round bottom flask, and dissolved in tetrahydrofuran (30 mL). To the stirred solution was added 25% sodium methoxide (11.50 g, 53 mmol) via an addition funnel over a 2 minute period. Next 4'-chloroacetophenone (6.83 g, 44 mmol) was added to the reaction dropwise over 5 minutes. After stirring overnight, 3N HCl (21 mL) was added. The organic layer was collected, washed with brine (75 mL), dried over $MgSO_4$, filtered, and concentrated in vacuo to give an orange solid. The solid was recrystallized from iso-octane/methylene chloride to give the dione (3.07 g): mp 158–161° C. M+H 292.

Step 2: Preparation of 1-[4-(methylsulfonyl)phenyl]-3,5-bis (4-chloroohenyl)-1H-pyrazole.

4-(Methylsulphonyl)phenylhydrazine hydrochloride (1.4 g, 6.2 mmol) is added to a stirred solution of 1,3-bis[4-chlorophenyl]propane-1,3-dione (1.6 g, 5.4 mmol) in a mixture of ethanol (50 mL), acetone and acetonitrile. The reaction is heated to reflux and stirred. After cooling to room temperature, the reaction mixture is concentrated in vacuo. The residue is taken up in ethyl acetate and washed with water and brine and dried over $MgSO_4$, filtered, and concentrated in vacuo to give 1-[4-(methylsulfonyl)phenyl]-3, 5-bis(4-chlorophenyl)-1H-pyrazole.

BIOLOGICAL EVALUATION

Rat Carrageenan Foot Pad Edema Test

The carrageenan foot edema test is performed essentially as described by Winter et al [*Proc. Soc. Exp. Biol. Med.*, 111, 544 (1962)]. Rats are dosed orally with compounds suspended in methylcellulose. One hour later a subplantar injection of 0.1 ml of 1% solution of carrageenan is administered and the volume of the injected foot is measured with a displacement plethysmometer. Three hours after the injection of the carrageenan the volume of the foot is again measured. The average foot swelling in a group of drug-treated animals is compared with that of a group of placebo-treated animals and the percentage inhibition of edema is determined (Otterness and Bliven, Laboratory Models for Testing NSAIDS, in Non-steroidal Anti-Inflammatory Drugs, (J. Lombardino, ed. 1985)). The compounds of Formula I should be active in reducing inflammation in the Carrageenan paw assay at a dosage of 30 mg per kg body weight.

Rat Carrageenan-induced Analgesia Test

The analgesia assay using rat carrageenan is performed essentially as described by Hargreaves et al (*Pain*, 32, 77, 1988). Rats are treated exactly as described above for the carrageenan foot pad edema test. At the end of the three hour period the rats are placed in a plexiglass container and a light shone directly on either the injected foot or on the contralateral uninjected foot. The time until the rat withdraws its foot is then measured. The withdrawal latency in seconds is determined for the control and drug treated groups and percent inhibition of the hyperalgesic foot withdrawal determined. The compounds of Formula I should be active in the analgesia assay at a dosage of 30 mg per kg body weight.

Evaluation of COX I and COX II activity in vitro

The compounds of this invention exhibited inhibition in vitro of COX II. The COX II inhibition activity of the compounds of this invention illustrated in the Examples was determined by the following methods.

a. Preparation of recombinant COX baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D. R. O'Reilly et al (*Baculovirus Expression Vectors: A Laboratory Manual* (1992)). Recombinant baculoviruses were isolated by transfecting 4 μg of baculovirus transfer vector DNA into SF9 insect cells (2×10e8) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors (0.5×10$^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX I and COX II activity:

COX activity was assayed as $PGE_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table XII.

TABLE XII

| Example | Human COX II $ID_{50}$ μM | Human COX I $ID_{50}$ μM |
| --- | --- | --- |
| 2 | <.1 | 8.5 |
| 2a | .2 | 13.6 |
| 2b | .3 | 19.1 |
| 2c | .5 | 2.1 |
| 2d | <.1 | 12.7 |
| 2e | .7 | >100 |
| 2g | <.1 | >100 |
| 3 | <.1 | 1.7 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered ner os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

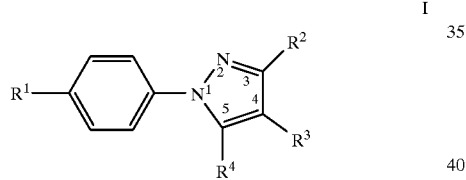

I wherein $R^1$ is sulfamyl;

wherein $R^2$ is aryl or heterocyclic; wherein $R^2$ is optionally substituted at a substitutable position with one or more radicals selected from halo, $C_1$–$C_{10}$-alkoxy, $C_1$–$C_{20}$-alkyl, nitro, $C_1$–$C_{10}$-alkylthio, amino, $C_1$–$C_{20}$-haloalkyl, hydroxyl, carboxyl, N-mono-$C_1$–$C_{20}$-alkylamino, N,N-di-$C_1$–$C_{20}$-alkylamino, cyano, $C_1$-Clo-alkoxycarbonyl and acylamino;

wherein $R^3$ is selected from hydrido, $C_1$–$C_{20}$-alkyl, $C_1$–$C_{20}$-haloalkyl, cyano, carboxyl, $C_1$–$C_{10}$-alkoxycarbonyl, amino, acyl, acylamino, halo and $C_1$–$C_{20}$-alkylsulfonylamino; and wherein $R^4$ is aryl or heterocyclic; wherein $R^4$ is optionally substituted at a substitutable position with one or more radicals selected from halo, $C_1$–$C_{10}$-alkoxy, $C_1$–$C_{20}$-alkyl, nitro, $C_1$–$C_{10}$-alkylthio, amino, $C_1$–$C_{20}$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

provided $R^4$ cannot be phenyl, 2-thienyl or substituted triazole, when $R^3$ is hydrido or bromo; further provided $R^2$ cannot be phenyl, or 2-thienyl, when $R^3$ is hydrido; and further provided one of $R^2$ and $R^4$ is heterocyclic;

or a pharmaceutically-acceptable salt thereof.

2. Compound of claim 1 wherein $R^1$ is sulfamyl;

wherein $R^2$ is aryl or heteroaryl; wherein $R^2$ is optionally substituted at a substitutable position with one or more radicals selected from halo, $C_1$–$C_6$-alkoxy, $C_1$–$C_6$-alkyl, nitro, $C_1$–$C_6$-alkylthio, amino, $C_1$–$C_6$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

wherein $R^3$ is selected from hydrido, $C_1$–$C_6$-alkyl, $C_1$–$C_6$-haloalkyl, cyano, carboxyl, $C_1$–$C_{10}$-alkoxycarbonyl, amino, acyl, acylamino, halo and $C_1$–$C_{20}$-alkylsulfonylamino; and wherein $R^4$ is aryl or heteroaryl; wherein $R^4$ is optionally substituted at a substitutable position with one or more radicals selected from halo, $C_1$–$C_6$-alkoxy, $C_1$–$C_6$-alkyl, nitro, $C_1$–$C_6$-alkylthio, amino, $C_1$–$C_6$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

or a pharmaceutically-acceptable salt thereof.

3. Compound of claim 2 wherein $R^2$ is selected from phenyl, pyrryl, furyl, pyridyl, pyrimidyl, pyrazinyl, pyrazolyl, oxazolyl, isoxazolyl, imidazolyl, thiazyl, pyranyl and thienyl;

wherein $R^2$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl and acetamido;

wherein $R^3$ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH$—; and wherein $R^4$ is selected from phenyl, pyrryl, furyl, pyridyl, pyrimidyl, pyrazinyl, pyrazolyl, oxazolyl, isoxazolyl, imidazolyl, thiazyl, pyranyl and thienyl; wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl and acetamido;

or a pharmaceutically-acceptable salt thereof.

4. Compound of claim 3 selected from compounds, and their pharmaceutically-acceptable salts, of the group of compounds consisting of 4-[3-(4-pyridyl)-5-(4-chlorophenyl)-1H-pyrazol-1-yl]benzenesulfonamide;

4-[3-(2-thienyl)-5-(4-chlorophenyl)-1H-pyrazol-1-yl]benzenesulfonamide;

4-[3-(5-chloro-2-thienyl)-5-(4-chlorophenyl)-1H-pyrazol-1-yl]benzenesulfonamide;

4-[3-(2-furanyl)-5-(4-chlorophenyl)-1H-pyrazol-1-yl]benzenesulfonamide;

4-[3-(4-chlorophenyl)-5-(2-thienyl)-1H-pyrazol-1-yl]benzenesulfonamide;

4-[3-(4-chlorophenyl)-5-(4-pyridyl)-1H-pyrazol-1-yl]benzenesulfonamide; and

4-[3-(4-chlorophenyl)-5-(2-furanyl)-1H-pyrazol-1-yl]benzenesulfonamide.

5. A pharmaceutical composition comprising a therapeutically-effective amount of a compound and a pharmaceutically-acceptable carrier or diluent, said compound selected from a family of compounds of Formula I

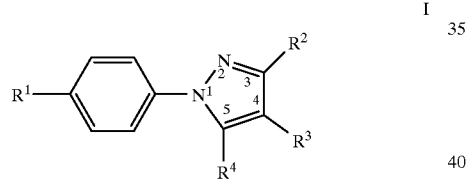

wherein $R^1$ is sulfamyl;

wherein $R^2$ is aryl or heterocyclic; wherein $R^2$ is optionally substituted at a substitutable position with one or more radicals selected from halo, $C_1$–$c_{10}$-alkoxy, $C_1$–$C_{20}$-alkyl, nitro, $C_1$–$C_{10}$-alkylthio, amino, $C_1$–$C_{20}$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

wherein $R^3$ is selected from hydrido, $C_1$–$C_{20}$-alkyl, $C_1$–$C_{20}$-haloalkyl, cyano, carboxyl, $C_1$–$C_{10}$-alkoxycarbonyl, amino, acyl, acylamino, halo and $C_1$–$C_{20}$-alkylsulfonylamino; and wherein $R^4$ is aryl or heterocyclic; wherein $R^4$ is optionally substituted at a substitutable position with one or more radicals selected from halo, $C_1$–$C_{10}$-alkoxy, $C_1$–$C_{20}$-alkyl, nitro, $C_1$–$C_{10}$-alkylthio, amino, $C_1$–$C_{20}$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

provided $R^4$ cannot be phenyl, 2-thienyl or substituted triazole, when $R^3$ is hydrido or bromo; further provided $R^2$ cannot be phenyl, or 2-thienyl, when $R^3$ is hydrido; and further provided one of $R^2$ and $R^4$ is heterocyclic; or a pharmaceutically acceptable salt thereof.

6. The composition of claim 5 wherein $R^1$ is sulfamyl;

wherein $R^2$ is aryl or heteroaryl; wherein $R^2$ is optionally substituted at a substitutable position with one or more radicals selected from halo, $C_1$–$C_6$-alkoxy, $C_1$–$C_6$-alkyl, nitro, $C_1$–$C_6$-alkylthio, amino, $C_1$–$C_6$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

wherein $R^3$ is selected from hydrido, $C_1$–$C_6$-alkyl, $C_1$–$C_6$-haloalkyl, cyano, carboxyl, $C_1$–$C_{10}$-alkoxycarbonyl, amino, acyl, acylamino, halo and $C_1$–$C_{20}$-alkylsulfonylamino; and wherein $R^4$ is aryl or heteroaryl; wherein $R^4$ is optionally substituted at a substitutable position with one or more radicals selected from halo, $C_1$–$C_6$-alkoxy, $C_1$–$C_6$-alkyl, nitro, $C_1$–$C_6$-alkylthio, amino, $C_1$–$C_6$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

or a pharmaceutically-acceptable salt thereof.

7. The composition of claim 6 wherein $R^2$ is selected from phenyl, pyrryl, furyl, pyridyl, pyrimidyl, pyrazinyl, pyrazolyl, oxazolyl, isoxazolyl, imidazolyl, thiazyl, pyranyl and thienyl;

wherein $R^2$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl and acetamido;

wherein $R^3$ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH$—;

wherein $R^4$ is selected from phenyl, pyrryl, furyl, pyridyl, pyrimidyl, pyrazinyl, pyrazolyl, oxazolyl, isoxazolyl, imidazolyl, thiazyl, pyranyl and thienyl;

wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl and acetamido;

or a pharmaceutically-acceptable salt thereof.

8. The composition of claim 7 wherein said compound is selected from compounds, and their pharmaceutically-acceptable salts, of the group consisting of 4-[3,5-bis(4-chlorophenyl)-1H-pyrazol-1-4-[3-(4-pyridyl)-5-(4-chlorophenyl)-1H-pyrazol-1-yl]benzenesulfonamide;

4-[3-(2-thienyl)-5-(4-chlorophenyl)-1H-pyrazol-1-yl]benzenesulfonamide;

4-[3-(5-chloro-2-thienyl)-5-(4-chlorophenyl)-1H-pyrazol-1-yl]benzenesulfonamide;

4-[3-(2-furanyl)-5-(4-chlorophenyl)-1H-pyrazol-1-yl]benzenesulfonamide;

4-[3-(4-chlorophenyl)-5-(2-thienyl)-1H-pyrazol-1-yl]benzenesulfonamide;

4-[3-(4-chlorophenyl)-5-(4-pyridyl)-1H-pyrazol-1-yl]benzenesulfonamide; and

4-[3-(4-chlorophenyl)-5-(2-furanyl)-1H-pyrazol-1-yl]benzenesulfonamide.

9. A therapeutic method of treating inflammation or an inflammation-related disorder in a subject, said method comprising administering to the subject having or susceptible to such inflammation or inflammation-related disorder, a therapeutically-effective amount of a compound of Formula I

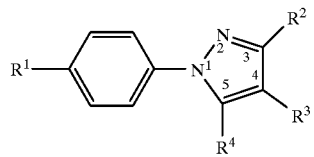

wherein $R^1$ is sulfamyl;

wherein $R^2$ is aryl or heterocyclic; wherein $R^2$ is optionally substituted at a substitutable position with one or more radicals selected from halo, $C_1$–$C_{10}$-alkoxy, $C_1$–$C_{20}$-alkyl, nitro, $C_1$–$C_{10}$-alkylthio, amino, $C_1$–$C_{20}$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

wherein $R^3$ is selected from hydrido, $C_1$–$C_{20}$-alkyl, $C_1$–$C_{20}$-haloalkyl, cyano, carboxyl, $C_1$–$C_{10}$-alkoxycarbonyl, amino, acyl, acylamino, halo and $C_1$–$C_{20}$-alkylsulfonylamino; and wherein $R^4$ is aryl or heterocyclic; wherein $R^4$ is optionally substituted at a substitutable position with one or more radicals selected from halo, $C_1$–$C_{10}$-alkoxy, $C_1$–$C_{20}$-alkyl, nitro, $C_1$–$C_{10}$-alkylthio, amino, $C_1$–$C_{20}$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

provided one of $R^2$ and $R^4$ is heterocyclic;

or a pharmaceutically acceptable salt thereof.

10. The method of claim 9 wherein $R^1$ is sulfamyl; wherein $R^2$ is aryl or heteroaryl; wherein $R^2$ is optionally substituted at a substitutable position with one or more radicals selected from halo, $C_1$–$C_6$-alkoxy, $C_1$–$C_6$-alkyl, nitro, $C_1$–$C_6$-alkylthio, amino, $C_1$–$C_6$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

wherein $R^3$ is selected from hydrido, $C_1$–$C_6$-alkyl, $C_1$–$C_6$-haloalkyl, cyano, carboxyl, $C_1$–$C_{10}$-alkoxycarbonyl, amino, acyl, acylamino, halo and $C_1$–$C_{20}$-alkylsulfonylamino; and wherein $R^4$ is aryl or heteroaryl; wherein $R^4$ is optionally substituted at a substitutable position with one or more radicals selected from halo, $C_1$–$C_6$-alkoxy, $C_1$–$C_6$-alkyl, nitro, $C_1$–$C_6$-alkylthio, amino, $C_1$–$C_6$-haloalkyl, hydroxyl, carboxyl, N-mono-$C_1$–$C_{20}$-alkylamino, N,N-di-$C_1$–$C_{20}$-alkylamino, cyano, $C_1$–$C_{10}$-alkoxycarbonyl and acylamino;

or a pharmaceutically-acceptable salt thereof.

11. The method of claim 9 wherein $R^2$ is selected from phenyl, pyrryl, furyl, pyridyl, pyrimidyl, pyrazinyl, pyrazolyl, oxazolyl, isoxazolyl, imidazolyl, thiazyl, pyranyl and thienyl; wherein $R^2$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl and acetamido; wherein $R^3$ is selected from hydrido, methyl, ethyl, propyl, isopropyl, butyl, isobutyl, tert-butyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, amino, acetyl, formyl, acetamido, fluoro, chloro, iodo, bromo and $CH_3SO_2NH$—; and wherein $R^4$ is selected from phenyl, pyrryl, furyl, pyridyl, pyrimidyl, pyrazinyl, pyrazolyl, oxazolyl, isoxazolyl, imidazolyl, thiazyl, pyranyl and thienyl; wherein $R^4$ is optionally substituted at a substitutable position with one or more radicals selected from fluoro, chloro, bromo, iodo, methoxy, ethoxy, propoxy, butoxy, isobutoxy, isopropoxy, methyl, ethyl, propyl, isopropyl, butyl, isobutyl, tert-butyl, nitro, methylthio, ethylthio, amino, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, carboxyl, N-methylamino, N-ethylamino, N-isopropylamino, N-propylamino, N-butylamino, N-isobutylamino, N-tert-butylamino, N-pentylamino, N,N-dimethylamino, N-methyl-N-ethylamino, cyano, methoxycarbonyl, ethoxycarbonyl, isopropoxycarbonyl, tert-butoxycarbonyl, propoxycarbonyl, butoxycarbonyl, isobutoxycarbonyl, pentoxycarbonyl and acetamido; or a pharmaceutically-acceptable salt thereof.

12. The method of claim 9 wherein said compound is selected from compounds, and their pharmaceutically-acceptable salts, of the group consisting of 4-[3-(4-pyridyl)-5-(4-chlorophenyl)-1H-pyrazol-1-yl]benzenesulfonamide;

4-[3-(2-thienyl)-5-(4-chlorophenyl)-1H-pyrazol-1-yl]benzenesulfonamide;

4-[3-(5-chloro-2-thienyl)-5-(4-chlorophenyl)-1H-pyrazol-1-yl]benzenesulfonamide;

4-[3-(2-furanyl)-5-(4-chlorophenyl)-1H-pyrazol-1-yl]benzenesulfonamide;

4-[3-(4-chlorophenyl)-5-(2-thienyl)-1H-pyrazol-1-yl]benzenesulfonamide;

4-[3-(4-chlorophenyl)-5-(4-pyridyl)-1H-pyrazol-1-yl]benzenesulfonamide; and

4-[3-(4-chlorophenyl)-5-(2-furanyl)-1H-pyrazol-1-yl]benzenesulfonamide.

13. The method of claim 9 for use in treatment of inflammation.

14. The method of claim 9 for use in treatment of an inflammation-associated disorder.

15. The method of claim 14 wherein the inflammation-associated disorder is arthritis.

16. The method of claim 14 wherein the inflammation-associated disorder is pain.

17. The method of claim 14 wherein the inflammation-associated disorder is fever.

* * * * *